US006047410A

United States Patent [19]

Dondero

[11] Patent Number: 6,047,410

[45] Date of Patent: Apr. 11, 2000

[54] GOGGLE FRAME AND ATTACHMENT SYSTEM

[75] Inventor: John D. Dondero, Ketchum, Id.

[73] Assignee: Eye Safety Systems, Inc., Sun Valley, Id.

[21] Appl. No.: 09/128,048

[22] Filed: Aug. 3, 1998

[51] Int. Cl.[7] ................................ A61F 9/02; G02C 5/22

[52] U.S. Cl. ....................... 2/426; 2/436; 2/449; 351/158

[58] Field of Search ................................ 2/426, 427, 428, 2/436, 438, 440, 452, 431, 451, 441, 443, 449, 450; 351/44, 158

[56] References Cited

U.S. PATENT DOCUMENTS

| | | | |
|---|---|---|---|
| 3,298,031 | 1/1967 | Morgan | 2/9 |
| 4,391,498 | 7/1983 | Rengstorff | 351/121 |
| 4,978,209 | 12/1990 | Ohba | 351/153 |
| 5,341,516 | 8/1994 | Keim | 2/452 |
| 5,410,763 | 5/1995 | Bolle | 2/436 |
| 5,495,623 | 3/1996 | Leoonardi | 2/431 |
| 5,511,251 | 4/1996 | Brakas | 2/452 |
| 5,642,178 | 6/1997 | Leonardi et al. | 351/111 |

*Primary Examiner*—John J. Calvert
*Assistant Examiner*—Tejash D Patel
*Attorney, Agent, or Firm*—Curtis L. Harrington

[57] ABSTRACT

An improved goggle system includes a goggle housing surroundably supporting one or two lenses, and further includes a hinged strap attachment member which is pivotally engaged to the goggle housing forward of the rearward most extent of the side lens or lenses. The hinged strap attachment member has a small shield member disposed generally toward the axis of pivot to protect the space between the hinge and the goggle, and also to provide a smooth interfit with the goggle when the hinge is displaced back toward the head of the wearer, as when the goggle is used without a helmet or other structure which would tend to pull outwardly rather than back against the head of the user. The hinges have sufficient flexibility matched with respect to sufficient pin length to enable the hinges to be rapidly and easily removed from the goggle, so that the goggle could be removed from the helmet or other support system when the goggles are needed elsewhere. An integrated, angled strap support post is provided on and integral with the goggle housing, which would normally lie underneath the hinge when the hinge is in place, to enable the user to quickly insert another strap when needed.

17 Claims, 3 Drawing Sheets

GOGGLE FRAME AND ATTACHMENT SYSTEM

FIELD OF THE INVENTION

The present invention relates to an improved goggle frame and attachment system and particularly to a goggle frame and system which offers multiple attachment methods and an ability to fit with wider helmets.

BACKGROUND OF THE INVENTION

The prior art describes many types and shapes of eye protection and goggles for a similarly wide variety of uses. In firefighting art, as well as other users of head wear, the eye wear protection may be supported by the head wear rather than the head directly. In the case of firefighting equipment, it is desired for the helmet to fit closely to the head to further isolate the wearer's head tissue from flames and hot gasses.

Goggles which fit over the helmet are needed not only because non-interference from goggle straps for fitting directly on the head are desired, but also to help keep up with the equipment as a unit and to make certain that the equipment operates as an integrated unit.

Goggles have advantages over face shields which make them more desirable for use in firefighting, including a smaller size less likely to be scratched, a fit closer to the face to either make a seal or to define a small space through which air flow can be controlled. Goggles also do a better job of sealing out debris and isolating the firefighter's eyes and facial tissues.

The use of goggles with head gear as an integrated unit is complicated by the size and shape of goggles. Good goggles have a sealing surface for close fit with the face. Strap support structures are typically located at the sides of the goggles and somewhat to the rear of the rearmost extent of the lenses. The location is usually rearward to promote stability with strapping worn on the head. However, the use of a goggle structure in conjunction with a helmet presents a length of strapping support which pulls less along the length of the wearer's head and more to the sides.

Forces which pull to the sides on goggles can destroy the usefulness of goggles which are meant to adhere closely to the face of the firefighter. Facial tissue can become exposed to the smoke and debris and can be dangerous. Danger can come both through harm to the firefighter, as well as through distraction from concentration of the emergency at hand.

What is therefore needed are goggles especially useful in hazardous or high stress situations, such as encountered in firefighting, and which can be supported by a firefighting helmet without being pulled outwardly from the face of the wearer. The operation of the needed goggle should not be dependent upon the size of the helmet, or the angle with which support from the helmet is derived. The needed goggle should be readily adjustable and readily useable without a helmet. Fittings which enable use with a helmet should be readily detachable.

SUMMARY OF THE INVENTION

The improved goggle system of the present invention includes a goggle housing surrounding one or two lenses, and further includes a pivoting side attachment member which is pivotally engaged to the goggle housing forward of the rearward most extent of the side lens or lenses. The hinged strap support has a small shield member disposed generally toward the axis of pivot to protect the space between the side attachment member and the goggle, and also to provide a smooth interfit with the goggle when the hinge is displaced back toward the head of the wearer, as when the goggle is used without a helmet or other structure which would tend to pull outwardly rather than back against the head of the user.

The hinges have sufficient flexibility matched with respect to sufficient pin length to enable the hinges to be rapidly and easily removed from the helmet or other support system when the goggles are needed elsewhere, yet always stay firmly attached when in use. An integrated, angled strap support post is provided on and integral with the goggle housing, which would normally lie underneath the hinge when the hinge is in place, to enable the user to quickly insert another strap when needed.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

Figure 1:
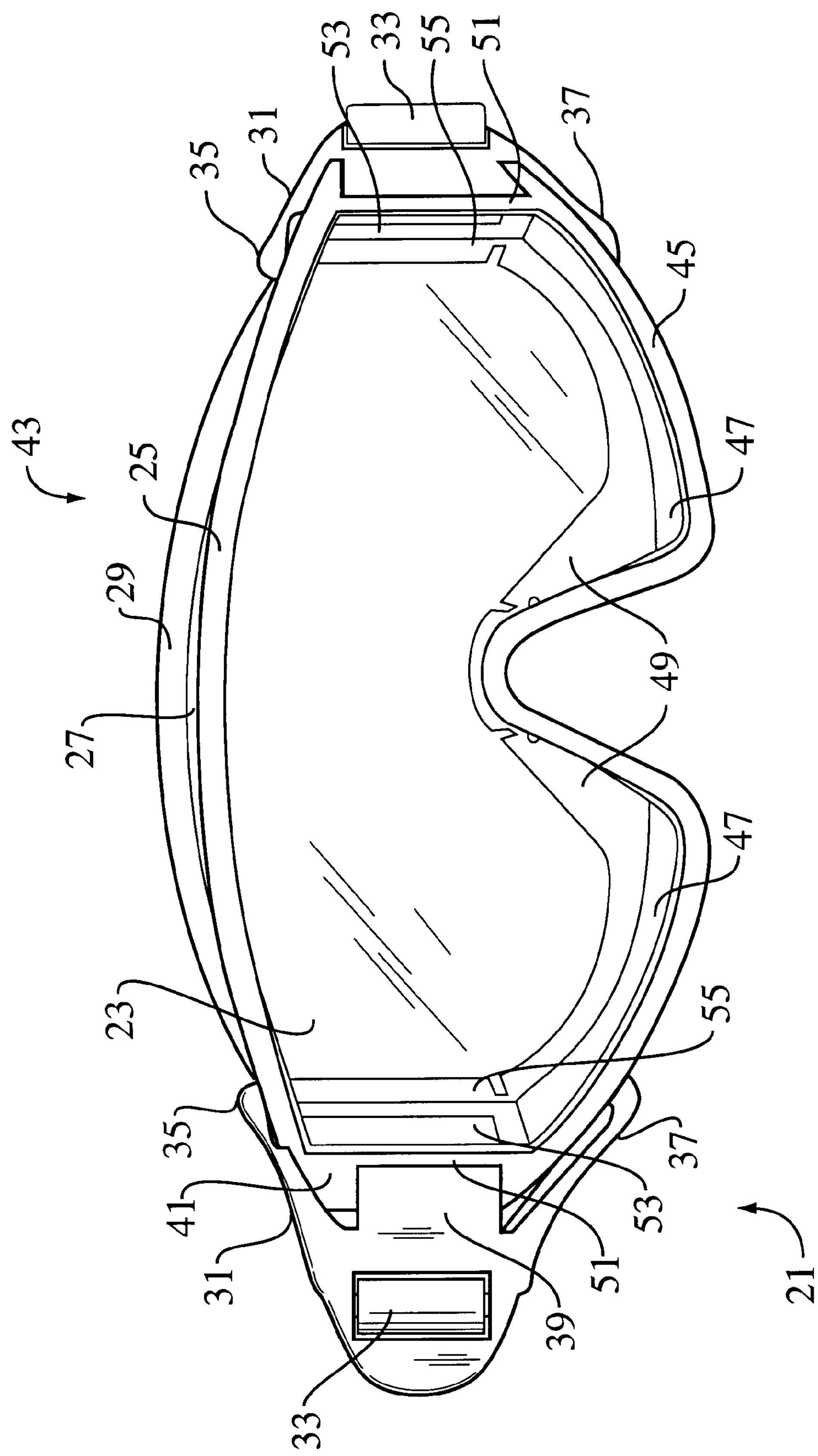
FIG. 1 is a front view of the goggle system of the invention, and illustrating prominently a pivoting side attachment member and shield extending toward the axis of pivot with one side attachment member folded back, and another folded forward in a position it would have if supported from a helmet (with a portion of a surface of the helmet shown in phantom.

A description of the inventive marker of the present invention is shown in FIG. 1. A goggle system 21 is seen in plan view and including a transparent clear shield or lens 23 mounted within a front frame 25 of the goggle system 21. An upper connecting web 27 is partially shown as connecting the front frame 25 to a rear seal member 29.

A pair of pivoting side attachment members 31 connect the ends of a strap 33, which is only partially seen as it extends through part of the pivoting side attachment members 31, to the goggle system 21. In the view of FIG. 1, the pivoting side attachment member 31 on the right is in a rearwardly directed position as it would be if the strap 33 were engaging the head of the user. The pivoting side attachment member 31 on the right is in a position as would be achieved if the strap 33 were supported from an object which would be wider than the head of the wearer, such as for example a helmet or other head equipment about which the unseen connecting portions of the strap 33 extended. The pivoting side attachment members 31 each include an upper pivot arm 35 and a lower pivot arm 37, as well as a small shield member 39, which is somewhat of a rectangular projection, and projection somewhat toward the axis of pivot of the pivoting side attachment members 31. When the pivoting side attachment members 31 are in the wide position, as seen at the left of the drawing of FIG. 1, the small shield member 39 helps to guard against projections entering into what would otherwise be a wide opening between the pivoting side attachment member 31 and a side portion 41 of the goggle housing 43. Goggle housing 43 includes side portion 41, front frame 25, upper connecting web 27, and rear seal member 29. As can be seen in FIG. 1, the side portion 41 of the goggle housing is preferably designed to compementarily accommodate the pivoting side attachment members 31 in a close relationship to the side portions 41 of the goggle system when the strap 33 is worn on the head or when the strap 33 is supported rearwardly.

Other features seen in FIG. 1 include lower frame 45, lower connecting web 47 and lower sealing member 49. Side frame portion 51, side web and strap slot portion 53 and side sealing member 55 can also be partially seen.

The upper pivot arm 35 and lower pivot arm 37 are shown as terminated in with a slight bulge away from the goggle housing 43, and which as will be shown, includes a thickening of material to support pivot pins (not yet seen) which extend into the upper web 27 and lower web 47 portions of the system 21, respectively. Note that the upper pivot arm 35 and lower pivot arm 37 terminate and will pivot along an axis of pivot which is forward to the rearward most extent of the lens 23. This enables wide support to be utilized, as shown at the left side of FIG. 1, but without being applied from a point so far rearward of the goggle housing 43 that it would tend to bend the goggle system 21 away from the face of the wearer.

Figure 2:
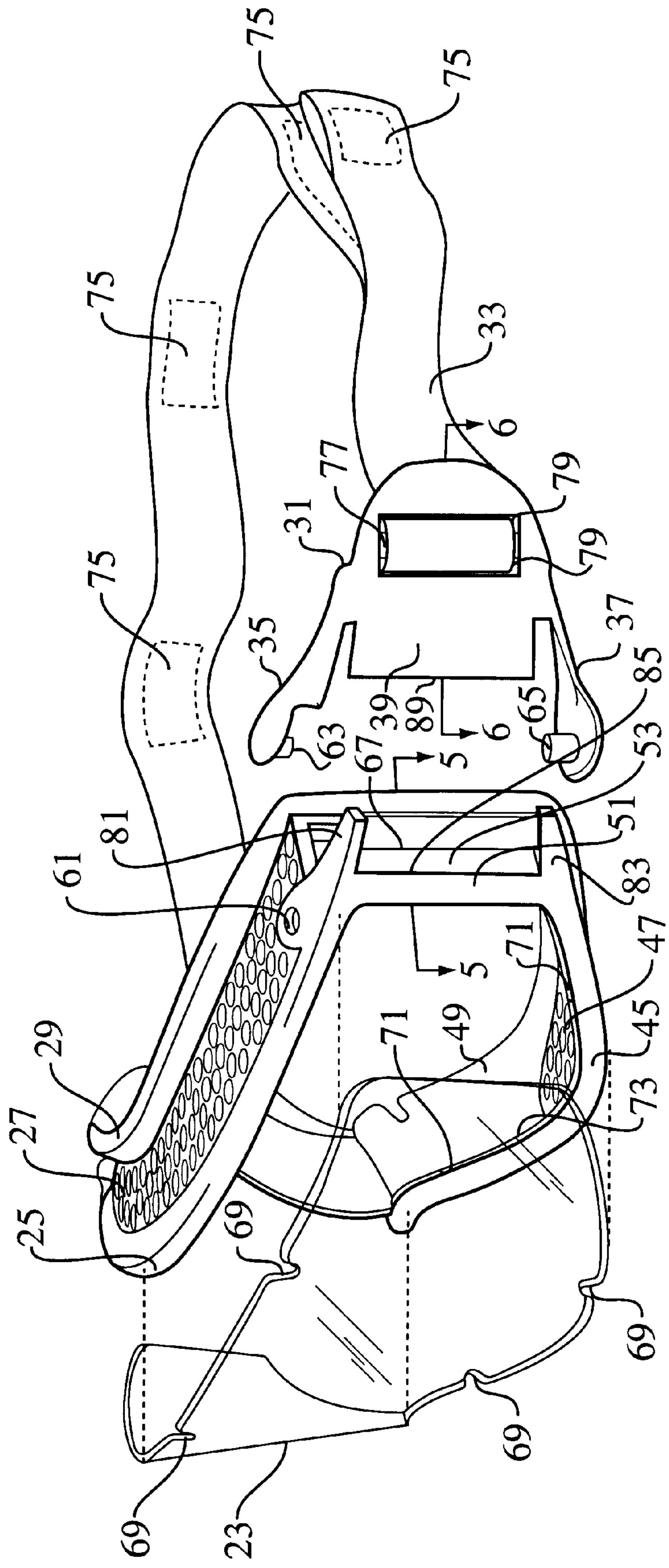
FIG. 2 is a front perspective exploded view illustrating the pivoting side attachment member removed and showing the pivot pins which extend into the goggle housing, the goggle lens displaced forwardly of the goggle housing, and the strap attachment structures which are integral to the goggle housing, and the complementary depression of the main goggle housing which interfits with the shield of the pivoting side attachment member.

Referring to FIG. 2, a side view of the goggle system 21 is illustrated with the pivoting side attachment member 31 in the foreground removed to show its component parts. At the top of the goggle housing 43, in a rearward continuation of the front frame 25 and extending into the area normally occupied by the connecting web 27, an upper abbreviated length pivot bore 61 is seen. Pivot bore 61 is immediately surrounded by smooth material to facilitate long and uninterrupted smooth pivoting action. At the end of the upper pivot arm 35, a downwardly extending generally cylindrical pivot pin 63 is oriented to enter the upper pivot bore 61 when the pivoting side attachment member 31 is engaged with the goggle housing 43. Similarly, the lower pivot arm 37 has an upwardly directed generally cylindrical upper pivot pin 65 for engagement into a bottom structure of the goggle housing 43 which will be shown.

Side web and strap slot portion 53 are better seen as two structures having a sharply angled slot 67 for interfitting of another goggle strap, similar to strap 33. Slot 67 angles back more than 45° from an entry point normal to the surface of the goggle housing 43 into which the slot 67 enters. The structure of the sharply angled slot 67 also enables tension fixation in the same manner as engagement with strap 33 with respect to pivoting side attachement members 31. Although it is not necessarily recommended to use two straps simultaneously, the side web and strap slot portion 53 enables the goggle housing 43 to be released from the pivoting side attachment members 31, especially to leave strap 33 connected to a helmet or the like, to then take the goggle housing 43 with lens 23 and thread a new strap through the side web and strap slot portion 53 for use directly on the head. Although only one pivoting strap connecting member 31 is prominently shown in FIG. 2, the other pivoting strap connecting member and other side of the goggle housing 43 is a mirror image and has the same structures.

Lens 23 is also shown as having a series of notches 69 which interfit with posts 71, two of which are seen as small cross members in a lens slot 73 which supports and interfits with the edge of the lens 23. Lens slot 73 exists in both the upper frame 25 and the lower frame 45. The posts 71 are used to better help the lens 23 to interlock into the upper and lower frames 25 and 45.

At the top connecting web 27 and lower connecting web 47 are seen a plurality of spaced apertures which are so numerous that they form a portion of the texture thereof. These apertures actually form a vertical air vent which promotes some movement of air flow in the goggle housing 43. It is an option to mount a fan motor in the top connecting web in order to help force air into the goggle housing 43 and behind the lens 23. This is an option not shown in FIG. 2, but the option is not impeded by the system 21 shown.

The strap 33 may have patches of one of hook and loop fastening members 75 for customized attachment to various points around the outside of a helmet. Attachment can be through snaps, grommets, gluing or even more permanent attachment. It is especially due to the most permanent attachment structures that the side web and strap slot portion 53 becomes more advantageous as the goggle housing 43 is detached from the pivoting side attachment members 31.

Also seen in FIG. 2 is a center post 77 which divides a strap opening into a pair of strap accommodation spaces 79. The center post comes out slightly above the surface of the pivoting side attachment members 31 in order to help the strap to stay positioned. When used with a strap, the center post 77 and strap accommodation spaces 79 enable a user to pull the loose and of strap 33 rearward to tighten and tension fix the portion of the strap depending from a helmet or head or other support structure, which tension stays fixed even if the loose end of the strap is released. This action can be accomplished if the structure to which the strap 33 engages is configured to work with strapping so that pulling the strapping through the structure is had from one side, while the other side is "tension fixed" and retains the tension against which it was pulled through the structure. This structure on the pivoting side attachement members 31 include center post 77 which has surfaces that extend beyond the surface of the pivoting side attachement members 31.

Note that the side frame portion 51, along with an upper extended length 81 of the upper frame 25, and a lower extended length 83 of the lower frame 45, defines a rectangular slot 85 into which the small shield member 39 interfits when the pivoting side attachment member 31 is folded back it its rearward most position. Since the small shield member 39 points generally in the direction of the axis of pivot, the pivoting of the pivoting side attachment members 31 keeps a leading edge 89 of the small shield member 39 near the goggle housing 43 to avoid opening up a space between the pivoting side attachment members 31 and the goggle housing 43.

Figure 4:
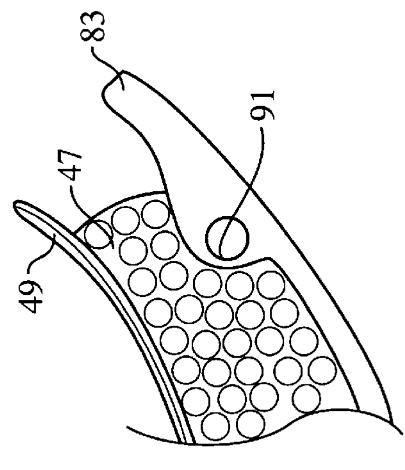
FIG. 4 is an upward view looking into the bottom of the goggle housing and better illustrating the lower pivot aperture.
Figure 3:
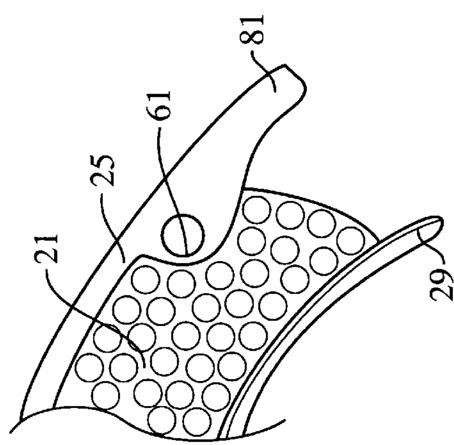
FIG. 3 is a downward view onto the top of the right side of the goggle housing and better illustrating the upper pivot aperture.

Referring to FIG. 3, a downward view onto the top of the right side of the goggle housing 43 better illustrates the upper pivot aperture 61 and surrounding structures. Referring to FIG. 4, an upward view looking into the bottom of the goggle housing 43 and better illustrating a shallow lower pivot bore 91 which is in alignment with the upper pivot aperture 61.

Figure 5:
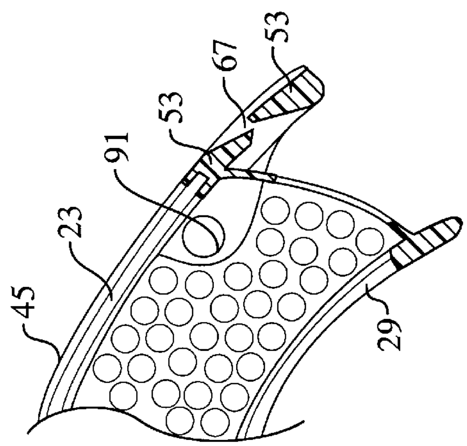
FIG. 5 is a sectional view taken along line 5—5 of FIG. 2 and illustrating the strap retention members of the goggle housing.

FIG. 5 is a sectional view taken along line 5—5 of FIG. 2 and illustrates the strap retention members of the goggle housing 43, including side web and strap slot portion 53 and sharply angled slot 67.

Figure 6:
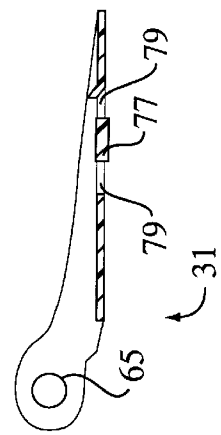
FIG. 6 is a sectional view taken along line 6—6 of FIG. 2 and illustrating a cross sectional view of the goggle strap supporting structures which are integral to the goggle housing.

Referring to FIG. 6, a sectional view taken along line 6—6 of FIG. 2 illustrates a cross sectional view of the goggle strap supporting structures, including center post 77 which extends slightly above the surface of the pivoting side attachment member 31 to better grasp the strap 33.

While the present invention has been described in terms of a set of goggles, goggle housing and support system to facilitate use of eye protection head wear with or without a helmet, one skilled in the art will realize that the structure and techniques of the present invention can be applied to many similar structures. The present invention may be applied in any situation where the lateral extent of a securing force may vary from application to application, but where an object is to be secured without significantly breaking contact due to a lateral component of the support force. The invention is especially useful where a removable holding structure facilitates use with a wider based securing system and where removal and reinstallation installation with respect to the securing system frees the supported structure to garner other support through additional structures located on the supported structure.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A goggle support comprising:

a goggle housing having at least one central opening for accepting at least one of a lens and shield, and including a first end and a second end;

a first attachment member having a pair of spaced apart collinear pivoting engagement structures for engaging said goggle housing nearer said first end of said goggle housing than said second end of said goggle housing, for supporting said goggle housing and including a first strap engagement structure to facilitate tension fixed engagement of said first strap engagement structure with a single length of a first strap portion threaded through said first strap engagement portion when said first strap engagement structure is in a rearward position and to facilitate release of said single length of said first strap portion when said first strap engagement structure is pivoted to a forward position; and a second attachment member having a pair of spaced apart collinear pivoting engagement structures for engaging said goggle housing nearer said second end of said goggle housing than said first end of said goggle housing, for supporting said goggle housing and including a second strap engagement structure to facilitate tension fixed support engagement of said second strap engagement structure with a single length of a second strap portion threaded through said second strap engagement portion when said second strap engagement structure is in a rearward position and to facilitate release of said single length of said second strap portion when said second strap engagement structure is pivoted to a forward position.

2. The goggle support recited in claim 1 and wherein both said first and said second attachment members contain a small shield member extending toward an axis of pivot of said of collinear pivoting engagement structures.

3. The goggle support recited in claim 2 wherein said goggle housing has a first space nearer said first end of said goggle housing than said second end and complementary to said small shield member of said first attachment member, and a second space nearer said second end of said goggle housing that said first end and complementary to said small shield member of said second attachment member.

4. The goggle support recited in claim 3 wherein said goggle housing includes a goggle strap opening adjacent each of said first and said second spaces.

5. The goggle support recited in claim 1 wherein said pair of collinear pivoting engagement structures of each attachment member further comprise a pair of spaced apart pivot arms each having oppositely disposed pivot pins directed toward each other, and wherein said goggle housing includes a pair of aligned pivot bores each engaged with a respective one of said pivot pins to enable said attachment members to pivot with respect to said goggle housing.

6. The goggle support recited in claim 1 wherein said goggle housing includes an upper and lower frame for engaging said lens, an upper connecting web connected to said upper frame and a lower connecting web connecting to said lower frame, and an upper rear seal member attached to said upper connecting web and a lower rear sealing member attached to said lower connecting web.

7. The goggle support recited in claim 6 and further comprising a lens supported by said upper and lower frames.

8. The goggle support recited in claim 7 and wherein said upper and lower frames include a lens slot, and wherein said lens is supported in said lens slot.

9. The goggle support recited in claim 1 and further comprising a lens supported by goggle frame.

10. The goggle support recited in claim 1 and wherein said goggle housing includes an upper and lower frame, each having a lens slot for engaging said lens, each of said lens slots having a plurality of posts within the slot and extending across the slot, and wherein said lens has a corresponding plurality of notches engaging said posts to better secure said lens with respect to said goggle housing.

11. The goggle support recited in claim 1 wherein said goggle housing includes a first goggle strap opening adjacent said first attachment member and a second goggle strap opening adjacent said second attachment member.

12. The goggle support recited in claim 11 wherein said first and said second goggle strap openings angle sharply into said goggle support for facilitating tension fixation of a strap with respect to said goggle support.

13. A goggle support comprising:

a goggle housing having at least one central opening for accepting at least one of a lens and shield, and including a first end and a second end;

a first attachment member having a pair of spaced apart collinear pivoting engagement structures for engaging said goggle housing nearer said first end of said goggle housing than said second end of said goggle housing, for supporting said goggle housing and including a first strap engagement structure to facilitate tension fixed engagement of said first strap engagement structure with a first strap portion; and a second attachment member having a pair of spaced apart collinear pivoting engagement structures for engaging said goggle housing nearer said second end of said goggle housing than said first end of said goggle housing, for supporting said goggle housing and including a second strap engagement structure to facilitate tension fixed support engagement of said second strap engagement structure with a second strap portion and wherein said first and second attachment member engage said goggle housing forward of said at least one central opening for accepting at least one of a lens and shield.

14. A goggle support comprising:

a goggle housing having at least one central opening for accepting at least one of a lens and shield, and including a top frame portion and a bottom frame portion a first side frame portion and a second side frame portion, spaced apart from said first side frame portion, said first and second side frame portions extending between said top frame portion and said bottom frame portion;

a first pivoting side attachment member pivotally attached to said goggle housing for pivotally engaging said goggle housing forward of said first side frame portion; and a second pivoting side attachment member pivotally attached to said goggle housing for pivotally engaging said goggle housing forward of said second side frame portion; said first and said second pivoting side attachment members for enabling said goggle housing to be supported from structures adjacent said goggle housing.

15. The goggle support recited in claim 14 wherein each of said first and second pivoting side attachment members include a strap engagement structure to facilitate enable support engagement of said strap engagement structure with a strap.

16. The goggle support recited in claim 14 wherein said goggle housing includes a first goggle strap opening adjacent said first side frame portion and a second goggle strap opening adjacent said second side frame portion.

17. A goggle support comprising:

a goggle housing having at least one central opening for accepting at least one of a lens and shield, and including a first end and a second end;

a first attachment member having a pair of spaced apart collinear pivoting engagement structures for engaging said goggle housing nearer said first end of said goggle housing than said second end of said goggle housing, for supporting said goggle housing and including a first strap tension fixation means for enabling a first strap engaged therewith to be tension adjusted by pulling on a free end of said first strap and to be freed from tension fixation by pivoting said first attachment member outward away from said goggle housing; and a second attachment member having a pair of spaced apart collinear pivoting engagement structures for engaging said goggle housing nearer said second end of said goggle housing than said first end of said goggle housing, for supporting said goggle housing and including a second strap tension fixation means for enabling a second strap engaged therewith to be tension adjusted by pulling on a free end of said second strap and to be freed from tension fixation by pivoting said second attachment member outward away from said goggle housing.

* * * * *